United States Patent [19]

Markert et al.

[11] Patent Number: 5,504,066
[45] Date of Patent: Apr. 2, 1996

[54] PENTENE DERIVATIVES, THEIR PRODUCTION AND USE

[75] Inventors: Thomas Markert, Duesseldorf; Volker Porrmann, Hilden; Klaus Bruns, Krefeld, all of Germany

[73] Assignee: Henkel Kommanditgesellschaft auf Aktien, Duesseldorf, Germany

[21] Appl. No.: 318,863

[22] Filed: Oct. 18, 1994

[30] Foreign Application Priority Data

Apr. 18, 1992 [DE] Germany ............ 42 12 941.9

[51] Int. Cl.⁶ ........................................... A61K 7/46
[52] U.S. Cl. .................... 512/8; 568/379; 568/838; 568/446; 568/348
[58] Field of Search .............. 512/8; 568/379, 568/838, 446, 348

[56] References Cited

U.S. PATENT DOCUMENTS

| | | | |
|---|---|---|---|
| 3,903,174 | 9/1975 | Comer et al. | 260/617 R |
| 4,610,813 | 9/1986 | Schulte-Elte et al. | 512/8 |
| 4,696,766 | 9/1987 | Naipawer | 568/838 |
| 5,288,701 | 2/1994 | Baudin | 512/8 |

FOREIGN PATENT DOCUMENTS

| | | | |
|---|---|---|---|
| 0155591 | 9/1985 | European Pat. Off. | 512/8 |
| 0466019 | 1/1992 | European Pat. Off. | 512/8 |
| 2513996 | 9/1976 | Germany | 512/8 |
| 0266347 | 3/1989 | Germany | 512/8 |
| 55-36423 | 3/1980 | Japan | 512/8 |
| 9201242 | 12/1992 | WIPO | 512/8 |

OTHER PUBLICATIONS

E. T. Morris, Dragoco Report 1983 (30), 40.

B. M. Lawrence, B. D. Mookherjee, B. J. Willis (Ed.): "Flavors and Fragrances: A World Perspective"; Elsevier Publishers, Amsterdam 1988.

J. Am. Chem. Soc. 1959, 81, 3379.

*Primary Examiner*—James H. Reamer
*Attorney, Agent, or Firm*—Wayne C. Jaeschke; John E. Drach; Henry E. Millson, Jr.

[57] ABSTRACT

The invention concerns pentene derivatives of the general formula (I), in which, independently of each other, $R^1$ is hydrogen or a methyl group, $R^2$ and $R^3$ are hydrogen or an alkyl group with 1 to 5 C-atoms, $R^4$ is hydrogen or a $CHR^5R^6$ group ($R^5$ and $R^6$ being hydrogen or an alkyl group with 1 to 6 C-atoms) and X is a CO or CHOH group, with the provision that (a) at least one of the groups $R^2$ and $R^3$ is an alkyl group and (b) 2-methyl-4-(2,2,3-trimethyl-3-cyclopenten-1-yl)-4-penten-1-ol is excluded. Such compounds are odoriferous substances with interesting fragrances and high diffusion power.

14 Claims, No Drawings

5,504,066

PENTENE DERIVATIVES, THEIR PRODUCTION AND USE

BACKGROUND OF THE INVENTION

1. Field of the Invention

This application is a 371 of PCT/EP 93/00883 Apr. 13, 1993.

This invention relates to new pentene derivatives, to a process for their production and to their use as fragrances.

2. Statement of Related Art

Going by demand, many natural fragrances are available in totally inadequate quantities. In perfumistic terms, sandalwood oil is particularly desirable and valuable. It is obtained by steam distillation from the heartwood of the sandalwood tree, a tropical semi-parasite which occurs in India and Malaysia. Heartwood appears after about 10 years and only begins to develop more quickly in 20-year-old trees. Fully grown trees are uprooted after 30 to 60 years because the roots are particularly rich in pleasantly smelling heartwood (E. T. Morris, *Dragoco Report* 1983 (30), 40). Accordingly, it is understandable why fragrance research is constantly endeavoring to develop suitable substitutes for natural sandalwood oil.

The focal points in the development of suitable substitutes for natural sandalwood oil are outlined by R. E. Naipower in a review (in: B. M. Lawrence, B. D. Mookherjee, B. J. Willis (Ed.): *"Flavors and Fragrances: A World Perspective"*; Elsevier Publishers, Amsterdam 1988). Alcohols containing a 2,2,3-trimethyl-3-cyclopentenyl group, including inter alia 2-methyl-4-(2,2,3-trimethyl- 3-cyclopenten-1-yl)-4-penten-1-ol, are known from EP 155 591 B1.

It is clear from the above context that there is a constant demand in the fragrance industry for new fragrances with interesting perfume notes in order to extend the range of naturally available fragrances and to make the necessary adaptations to varying fashion trends and to be able to meet the steadily growing demand for odor enhancers for products of everyday use, such as cosmetics and cleaning compositions.

In addition, there is generally a constant demand for synthetic fragrances which can be produced favorably in a consistent quality and which have desirable olfactory properties, i.e. which have pleasant, close-to-nature and qualitatively novel odor profiles of sufficient intensity and which are capable of favorably influencing the small of cosmetic and consumer goods. Accordingly, the problem addressed by the present invention was to provide new compounds which would have characteristic new odor profiles and, at the same time, high persistence, intensity of odor and emanative power.

DESCRIPTION OF THE INVENTION

It has now been found that the compounds corresponding to general formula (I) excellently satisfy the above-mentioned requirements in every respect and may advantageously be used as fragrances having differently nuanced odor notes with high persistence. In particular, it has been found that the compounds corresponding to general formula (I) have an improved intensity of odor, i.e. develop their effect in relatively low concentrations, by comparison with known structurally related compounds.

Accordingly, the present invention relates to pentene derivatives corresponding to general formula (I):

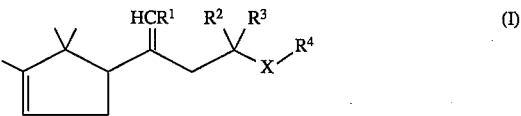

in which—independently of one another—the substituent $R^1$ is hydrogen or a methyl group, the substituents $R^2$ and $R^3$ are hydrogen or an alkyl group containing 1 to 5 carbon atoms, the substituent $R^4$ is hydrogen or a group $CHR^5R^6$, where the substituents $R^5$ and $R^6$ are hydrogen or an alkyl group containing 1 to 6 carbon atoms, and X is a group CO or a group CHOH, with the proviso that (a) at least one of the substituents $R^2$ or $R^3$ is an alkyl group and (b) 2-methyl-4-(2,2,3-trimethyl-3-cyclopenten-1-yl)-4-penten-1-ol is excluded.

Pentene derivatives (I), in which the substituents $R^2$ and $R^3$ are both alkyl groups, are particularly preferred. They are distinguished by improved intensity of odor in relation to the corresponding derivatives in which the two substituents $R^2$ and $R^3$ are hydrogen. Compounds (I) in which the substituents $R^2$ and $R^3$ are methyl or ethyl are especially preferred. Of these compounds, (a) 3,3-dimethyl-5-(2,2,3-trimethyl-3-cyclopenten-1-yl)-5-hexen-2-one (b) 3,3-dimethyl-5-(2,2,3-trimethyl-3-cyclopenten-1-yl)-5-hexen-2-ol (c) 2,2-dimethyl-4-(2,2,3-trimethyl-3-cyclopenten-1-yl)-1-penten-1-al (b) 2,2-dimethyl-4-(2,2,3-trimethyl-3-cyclopenten-1-yl)-4-penten-1-ol are particularly preferred.

According to the invention, pentene derivatives (I) in which the substituents $R^2$ and $R^3$ independently of one another are methyl or ethyl radicals are most particularly preferred.

In one particular embodiment of the invention, $R^4$ is hydrogen; in another particular embodiment, $R^4$ is methyl.

The new compounds (I) are prepared by syntheses known per se in organic chemistry. Two particularly attractive syntheses are described by way of Example in the following:

In a first variant, the allyl alcohol 2-(2,2,3-trimethyl-3-cyclopentenyl)-2-propen-1-ol is converted by Carroll reaction into ketones corresponding to general formula (I) where X is a carbonyl group. The Carroll reaction is understood to be the rearrangement of allyl alcohols into gamma-delta-unsaturated ketones. The allyl alcohol is converted, for example by reaction with acetoacetic ester, into the acetoacetic acid allyl ester which in turn is converted by (3,3)-sigmatropic rearrangement (Claisen rearrangement) into alpha-allylacetoacetic acid and then into the required gamma-delta-unsaturated ketone by thermal decarboxylation of the acid. The acetoacetic acid allyl ester may be used in bulk or may be formed in situ. Alternatively, the allyl alcohol may be converted with methyl isopropenyl ether—optionally in situ—into the corresponding allylvinyl ether which may then be rearranged to the ketones (I) in the same way as the acetoacetic acid allyl ester.

The ketones (I) thus obtained may then be alkylated in the usual way, for example with methyl iodide, at the carbon atoms adjacent the keto group. The quantity of alkylating agent used is determined by the desired degree of alkylation. 1 to 5 moles and preferably 1 to 3 moles of alkylating agent per mole of carbonyl compound and catalytic quantities of a phase transfer catalyst will normally be used. A mixture of, essentially, mono-, di- and trialkylation products is generally obtained as the crude product from which the individual compounds (I) may be isolated by standard methods, for example by distillation.

The carbonyl function of the alkylated carbonyl compounds may be reduced to the OH group in another reaction, for example using complex hydrides, such as lithium aluminium hydride or lithium or sodium borohydride. Other pentene derivatives corresponding to general formula (I) are obtained in this way.

In a second variant, compounds (I) in which X is a carbonyl group and the substituent $R^4$ is hydrogen are prepared by reaction of allyl alcohols corresponding to general formula (II):

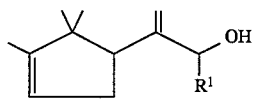
(II)

in which the substituent $R^1$ is hydrogen or a methyl group, with aldehydes corresponding to general formula (III):

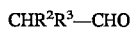
(III)

in which the substituents $R^2$ and $R^3$ independently of one another represent hydrogen or an alkyl group containing 1 to 5 carbon atoms, with the proviso that at least one of the substituents $R^2$ or $R^3$ is an alkyl group. In this reaction, an acetal is initially formed as an intermediate from compounds (II) and (III) and, after elimination of 1 molecule of alcohol, changes—again intermediately—into a vinylallyl ether which leads to the corresponding compound (I) according to the invention in a Claisen (3,3)—sigmatropic rearrangement. K. C. Brannock described this type of reaction starting out from special allyl alcohols and isobutyraldehyde in *J. Am. Chem. Soc.* 1959, 81, 3379. The reaction of the allyl alcohol with the aldehyde is generally carried out in the presence of a catalytically active quantity of an acid, for example a sulfonic acid, carboxylic acid or Lewis acid.

The aldehydes obtainable by this second variant may of course be further varied. Thus, other pentene derivatives corresponding to general formula (I) are obtained by reduction of their carbonyl functions to the OH group, for example with complex hydrides, such as lithium aluminium hydride or lithium or sodium borohydride. Finally, the aldehydes may be converted into other pentene derivatives (I) by reaction with the corresponding Grignard reagents.

Accordingly, the present invention also relates to a process for the production of pentene derivatives corresponding to general formula (I):

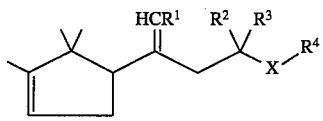
(I)

in which—independently of one another—the substituent $R^1$ is hydrogen or a methyl group, the substituents $R^2$ and $R^3$ are hydrogen or an alkyl group containing 1 to 5 carbon atoms, the substituent $R^4$ is hydrogen or a group $CHR^5R^6$, where the substituents $R^5$ and $R^6$ are hydrogen or an alkyl group containing 1 to 6 carbon atoms, and X is a group CO or a group CHOH, with the proviso that (a) at least one of the substituents $R^2$ or $R^3$ is an alkyl group and (b) 2-methyl-4-(2,2,3-trimethyl-3-cyclopenten-1-yl)-4-penten-1-ol is excluded, by (a) reaction of allyl alcohols corresponding to general formula (II):

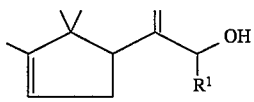
(II)

in which the substituent $R^1$ is hydrogen or a methyl group, with aldehydes corresponding to general formula (III):

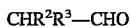
(III)

in which the substituents $R^2$ and $R^3$ independently of one another represent hydrogen or an alkyl group containing 1 to 5 carbon atoms, with the proviso that at least one of the substituents $R^2$ or $R^3$ is an alkyl group, or (b) alkylation of compounds corresponding to general formula (IV):

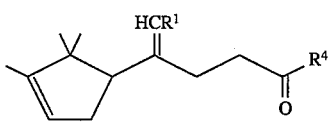
(IV)

in which the substituent $R^1$ is hydrogen or a methyl group, and $R^4$ is hydrogen or $CHR^5R^6$ wherein each of $R^5$ and $R^6$ is hydrogen or an alkyl group having from 1 to 6 carbon atoms, and, optionally, subsequent reduction of the carbonyl group to the OH function, for example with complex hydrides.

The compounds (I) according to the invention have remarkable odor properties. Accordingly, the present invention also relates to the use of compounds corresponding to general formula (I) as fragrances.

Compounds (I) in which X is a group CO are distinguished by a woody odor which increases in intensity through fresh, fruity aspects of bergamot and rhubarb. The same effect also occurs with the alcohols prepared from these ketones by reduction, i.e. with compounds (I) in which X is a group CHOH, the odor characteristic in their case being a strong sandalwood note with fruity aspects. Compounds in which the substituents $R^2$ and $R^3$ are alkyl radicals are distinguished in particular by a considerably higher intensity of odor compared with the corresponding compounds in which the substituents $R^2$ and/or $R^3$ are hydrogen, the new compounds developing their sandalwood note in relatively low concentrations in the head note of formulations.

In perfume compositions, the compounds corresponding to formula (I) enhance harmony and emanation and also persistence, the dosage being adapted to the particular fragrance note required taking the other constituents of the composition into consideration.

The fact that the pentene derivatives (I) would have sandalwood notes was not foreseeable and, accordingly, is further confirmation of the general observation that the olfactory properties of known fragrances do not allow any definitive conclusions to be drawn as to the properties of structurally related compounds because neither the mechanism of odor perception nor the influence of chemical structure on odor perception has been sufficiently researched so that it cannot normally be foreseen whether a change in the structure of known fragrances will lead to any change in the olfactory properties and whether these changes are considered to be positive or negative.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known fragrance ingredients, for example other fragrances of natural, synthetic or partly synthetic origin, essential oils and plant extracts. The range of natural fragrances can thus include both high-volatility and also medium-volatility and low-volatility components while the range of synthetic fragrances may include representatives of virtually every class of compounds. Examples are:

(a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil (b) alcohols, such as farnesol, geraniol, linalool, nerol, phenylethyl alcohol, rhodinol, cinnamic alcohol, sandalore [3-methyl-5-(2,2,3-trimethyl-cyclopent- 3-en-1-yl)-pentan-2-ol], sandela [3-isocamphyl-(5)-cyclohexanol]

(c) aldehydes, such as citral, Helional®, α-hexyl cinnamaldehyde, hydroxycitronellal, Lilial® [p-tert.butyl -α-methyldihydrocinnamaldehyde]-methylnonyl acetaldehyde (d) ketones, such as allylionone, α-ionone, β-ionone, isoraldein, methyl ionone (e) esters, such as allylphenoxyacetate, benzyl salicylate, cinnamyl propionate, citronellyl acetate, citronellyl ethoxylate, decyl acetate, dimethylbenzyl carbinyl acetate, ethyl acetoacetate, hexenyl isobutyrate, linalyl acetate, methyl dthydrojasmonate, vetiveryl acetate, cyclohexyl salicylate (f) lactones, such as gamma-undecalactone, 1-oxaspiro-[4.4]-nonan-2-one and various other components often used in perfumery, such as ketone musk, indole, p-methan-8-thiol-3-one, methyl eugenol, ambroxan.

It is also remarkable how the compounds corresponding to formula (I) round off and harmonize the odor notes of a broad range of known compositions without unpleasantly dominating them in any way. Those pentene derivatives (I) in which the two substituents $R^2$ and $R^3$ are alkyl groups are particularly prominent in this respect.

The compounds according to the invention contain chirality centers so that they may exist in various spatial forms. The compounds according to the invention accumulate as partly mixtures of the corresponding isomers in the course of typical syntheses and are used in this form as fragrances.

The compounds according to the invention or mixtures thereof may be used in fragrance compositions in quantities of 1 to 70% by weight, based on the mixture as a whole. Mixtures of compounds (I) according to the invention and compositions of this type may be used both for perfuming cosmetic preparations, such as lotions, creams, shampoos, soaps, salves, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations or tobacco. For perfuming the various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

The following Examples are intended to illustrate the invention without limiting it in any way.

EXAMPLES

1. Preparation of the precursors of the compounds according to the invention

Example 1

5-(2,2,3-Trimethyl-3-cyclopenten-1-yl)-5-hexen-2-one

Procedure:

In a 500 ml three-necked flask, 110 g (0.66 mole) of 2-(2,2,3-trimethyl-3-cyclopentenyl)-2-propenol (prepared from α-campholenaldehyde by condensation with formaldehyde and reduction with lithium aluminium hydride) were mixed with 172.3 g of acetoacetic acid ethyl ester (1.33 mole) and 1.5 g of N,N-dimethyl aminopyridine was added to the resulting mixture. The mixture was then heated with stirring for 2 hours to the reflux temperature and the ethanol released during the transesterification was distilled off. The temperature was then increased to 200° C. with removal of the ethanol released and was kept at that level for 6 hours. To complete the reaction, another 100 g of acetoacetic ester were added and the mixture was heated for 14 hours at 200° C.

Working up:

The reaction product was purified by distillation in a Vigreux column and in a spinning band column. Most of the distillate was obtained in a GC purity of 98% at head temperatures of 127°–135° C./15 mbar. The yield amounted to 14% of theoretical.

Characterization:

The IR spectrum of the product (film on NaCl) showed absorption bands at 1955, 1718 (C=O), 1639 (C=C), 1358 and 1160 cm$^{-1}$.

Odor:

Linalyl acetate, bergamot, basil note, flowery, woody.

2. Preparation of the compounds according to the invention

Example 2

3,3-Dimethyl-(2,2,3-trimethyl-3-cyclopenten-1-yl)-5-hexen-2-one

This Example illustrates the alkylation of the ketone of Example 1 with methyl iodide.

Procedure:

In a dry 1 liter reactor, 93.3 g (1.72 mole) of potassium hydroxide powder were suspended in 100 ml of absolute toluene while dry nitrogen was passed through, after which 0.83 g of the crown ether 18-crown-6 was added. 177 g (0.86 mole) of the ketone described in Example 1 were then added and 273.6 g (1.9 mole) of methyl iodide were introduced into the stirred mixture over a period of 3 hours. After the addition, the mixture was stirred overnight at room temperature.

Working up:

For working up, the reaction mixture was poured onto 1 l of ice water and the toluene phase was removed. The water phase was extracted with a total of 300 ml of ether. The combined organic phases were washed with 10% hydrochloric acid and sodium chloride solution, dried over sodium sulfate, filtered, concentrated and predistilled in a bulb tube. Further fine fractionation in a spinning band column produced 57.6 g of product melting at 75°–77° C./0.02 mbar (yield: 29% of the theoretical). The IR spectrum (film on NaCl) showed bands at 2956, 1717 (C=O), 1638 (C=C), 1460, 1360, 1068 and 894 cm$^{-1}$.
Odor:
Bergamot, rhubarb note, woody.

Example 3

3,3-Dimethyl-(2,2,3-trimethyl-3-cyclopenten-1-yl)-5-hexen-2-ol

This Example illustrates the selective reduction of the carbonyl group after alkylation of the ketone of Example 2 to the OH function.
Procedure:
15 g (0.4 mole) of sodium boranate in 200 ml of ethanol were introduced into a 1 liter three-necked flask. A solution of 117 g (0.5 mole) of the ketone of Example 2 was then added to the suspension over a period of 2 hours, after which the mixture was stirred for another hour.
Working up:
To destroy excess sodium boranate, 150 ml of water were added and the mixture was stirred overnight. It was then extracted with ether, the ether phases were washed with water until neutral and then dried over potassium carbonate. After filtration and concentration, the product was predistilled through a bulb tube and the crude product obtained (96 g) was then subjected to fractional distillation in a spinning band column. The main fraction of 68 g (=37.5% of the theoretical) was obtained at head temperatures of 87° to 95° C./0.1 mbar. The gas chromatogram showed an isomer mixture, the two main peaks making up 65% of the mixture.
Characterization:
The IR spectrum (film on NaCl) showed bands at 3367 (OH), 2958, 1637 (C=C), 1462, 1375, 1361 and 891 cm$^{-1}$.
Odor:
Sandalwood.

Example 4

2,2-Dimethyl-4-(2,2,3-trimethyl-3-cyclopenten-1-yl)-4-penten-1-al

This Example illustrates the reaction of an allyl alcohol with an aldehyde. Compounds (I) in which X is a group CO and R$^4$ is hydrogen are obtained in this variant.
Procedure:
30 g (0.18 mole) of 2-(2,2,3-trimethyl-3-cyclopenten-1-yl)-2-propen-1-ol (prepared from α-campholenaldehyde by condensation with formaldehyde and reduction of the aldehyde group) were introduced with 72 g (1 mole) of isobutyraldehyde and 1.5 g of pivalic acid into a 250 ml autoclave equipped with a lift stirrer. The autoclave was purged with nitrogen and then closed. It was heated to 190° C., a pressure of 18 bar being spontaneously established. The mixture was then heated under these conditions for 7 hours.
Working up:
After cooling, the excess isobutyraldehyde was distilled off and the residue of 60 g was distilled in a 12 cm Vigreux column. 21 g of distillate were obtained and were further purified in a spinning band column. The main fraction of 12.1 g (28% of the theoretical) distilled over at a temperature of 78°–80° C./0.04 mbar; it had a GC purity of 84%.
Characterization:
The IR spectrum (film on NaCl) showed bands at 2958, 2928 (H—CO), 1726 (CH=O), 1636 (C=C), 1467, 1362, 1194 and 900 cm$^{-1}$.
Odor:
Flowery, fruity, woody, sandalwood note:

Example 5

2,2-Dimethyl-4-(2,2,3-trimethyl-3-cyclopenten-1-yl)-4-penten-1-ol

This Example illustrates the selective reduction of the carbonyl group of the aldehyde of Example 4 to the OH function.
Procedure:
2 g (0.05 mole) of sodium boranate in 100 ml of ethanol were introduced into a 250 ml three-necked flask. A solution of 15 g (0.068 mole) of the aldehyde of Example 4 was then continuously added to the suspension and, after the mildly exothermic reaction had abated, the mixture was stirred for another hour.
Working up:
The reaction mixture was poured onto ammonium chloride solution/ice and extracted with ether. The organic phases were dried over sodium sulfate, filtered and concentrated. After preliminary distillation through a bulb tube (air bath temperature: 140° C.), the crude product was further purified in a spinning band column. The main fraction of 5.9 g was isolated at head temperatures of 82°–84° C./0.05 mbar (39% of the theoretical; GC purity: 95%).
Characterization:
The IR spectrum (film on NaCl) showed bands at 3368 (OH), 2955, 1634 (C=C), 1464, 1384, 1045 (C—O), 898 and 803 cm$^{-1}$.
Odor:
Fruity, sandalwood.

Example 6

3,3-Dimethyl-5-(2,2,3-trimethylcyclopent-3-en-1-yl)-hex-5-en-2-ol

Procedure:
In a dry 500 ml three-necked flask, 3.6 g (0.15 mole) of magnesium chips (99.5%, Riedel de Haen) were suspended in 100 ml of anhydrous ether and 21.6 g (0.15 mole) of iodomethane (99%, Fluka) were added dropwise at such a rate that, after the reaction had started, the mixture was kept under constant reflux (approx. 25 minutes). A solution of 22.0 g (0.1 mole) of the aldehyde (71%) prepared in accordance with Example 4 in 100 ml of ether was continuously added dropwise in the absence of moisture to the Grignard reagent thus prepared so that, during the dropwise addition, the reaction mixture was kept boiling by the heat of reaction released (approx. 20 minutes). After the addition, the mixture was stirred for another 4 hours at room temperature.
Working up:
The mixture was poured onto 500 ml of ice-cold saturated ammonium chloride solution and stirred for 30 minutes. The ether phase was separated off and the water phase was repeatedly extracted with ether. The combined ether phases were washed with saturated sodium chloride solution until neutral, dried over potassium carbonate, concentrated and distilled through a bulb tube. The distillate of 20 g (GC purity 85%) was fractionated in a spinning band column. The main fraction of 12 g (71% of theoretical) was obtained at head temperatures of 104°–106° C./0.05 mbar (GC purity of the diastereomer mixture: 99.7%).
Analysis:
IR spectrum (film on NaCl) shows absorption bands at 3387 (—OH), 3075, 3033, 2958, 1633 (C=C), 1463, 1383, 1361 (dimethyl), 1092 (C—O) and 898 cm$^{-1}$.

Odor:
Woody, fruity, sandalwood.

3. Composition Example 1

| Tobacco base | Parts by weight |
|---|---|
| Benzyl acetate | 150 |
| Atrinon (Henkel) | 150 |
| Geraniol | 120 |
| Vetiveryl acetate brut | 100 |
| Cedrenol | 50 |
| Cedarwood oil Florida | 50 |
| DPG | 40 |
| Oak moss res. | 40 |
| Guaiyl acetate | 30 |
| Cyclamber (Henkel) | 30 |
| Isoraldein 70 | 30 |
| Benzophenone | 30 |
| Patchouli oil | 30 |
| Olibanum res. | 25 |
| Cyclohexyl salicylate (Henkel) | 25 |
| Bergamot oil | 20 |
| Lavender oil | 20 |
| β-Naphthyl methylketone | 20 |
| Coumarin | 20 |
| Vanillin | 10 |
| Cinnamaldehyde | 10 |
| | 1000 |

Replacement of the 40 parts of dipropylene glycol (DPG) in the above mixture by 40 parts of 3,3-dimethyl-5-(2,2,3-trimethylcyclopent-3-en-1-yl)-hex-5-en-2-ol (Example 6) ideally combines woody and dry-spicy aspects of this base and provides the composition with a musk note. These effects cannot be achieved either by conventional sandalwood notes or by the known synthetic musk fragrances.

4. Composition Example

| Fancy fougere (fern) | Parts by weight |
|---|---|
| Boisambrene forte (Henkel) | 150 |
| Bergamot oil maroc. | 100 |
| Lavandin oil grosso | 100 |
| Jasmacyclat (Henkel) | 100 |
| Citronellol pure | 80 |
| Isoraldein 70 | 80 |
| Citral | 50 |
| DPG | 45 |
| Rosemary oil | 40 |
| Oak moss abs. | 30 |
| Orange oil light | 30 |
| Linalool | 30 |
| Ylang Ylang IP | 30 |
| Vetiver oil | 20 |
| Geranium oil Bourbon | 20 |
| Lavender abs. | 20 |
| Cinnamon leaf oil | 15 |
| Coriander oil | 15 |
| Thyme oil | 15 |
| Patchouli oil | 10 |
| Ciste abs. | 10 |
| Carnation oil | 5 |
| Motherwort oil | 5 |
| | 1000 |

If the 45 parts of dipropylene glycol in the above formulation are replaced by the same quantity of the 2,2-dimethyl-4-(2,2,3-trimethyl-cyclopent-3-en-1-yl)-pent-4-en-1-ol prepared in accordance with Example 5, the perfume is given intensive and long-lasting balsamy, musk-like undertones and a fruity top-note which enhances the naturalness of the overall impression.

What is claimed is:

1. A compound of the formula I

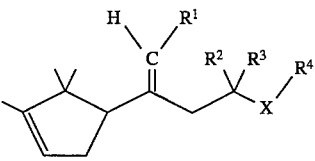

wherein $R^1$ is hydrogen or a methyl group, each of $R^2$ and $R^3$ is an alkyl group having from 1 to 5 carbon atoms, $R^4$ is hydrogen or $CHR^5R^6$ wherein each of $R^5$ and $R^6$ is hydrogen or an alkyl group having from 1 to 6 carbon atoms, and X is CO or a CHOH group with the proviso that at least one of $R^2$ and $R^3$ is an alkyl group having from 1 to 5 carbon atoms.

2. A compound of claim 1 wherein each of $R^2$ and $R^3$ is independently a methyl or an ethyl group.

3. A process for making a compound of the formula I

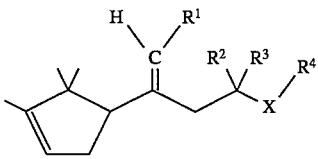

wherein $R^1$ is hydrogen or a methyl group, each of $R^2$ and $R^3$ is hydrogen or an alkyl group having from 1 to 5 carbon atoms, $R^4$ is hydrogen or $CHR^5R^6$ wherein each of $R^5$ and $R^6$ is hydrogen or an alkyl group having from 1 to 6 carbon atoms, and X is a CHOH group with the proviso that at least one of $R^2$ and $R^3$ is an alkyl group having from 1 to 5 carbon atoms which comprises the steps of: (1) reacting a ketone of the formula IV

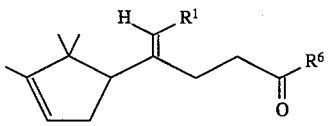

with an alkyl halide having from 1 to 5 carbon atoms and, (2) reducing the carbonyl group of the alkylated ketone formed in step (1) with a complex hydride reducing agent.

4. A fragrance composition comprised of from about 1% to about 70% by weight of a compound of the formula I

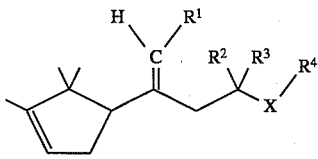

wherein $R^1$ is hydrogen or a methyl group, each of $R^2$ and $R^3$ is an alkyl group having from 1 to 5 carbon atoms, $R^4$ is hydrogen or $CHR^5R^6$ wherein each of $R^5$ and $R^6$ is hydrogen or an alkyl group having from 1 to 6 carbon atoms, and X is CO or a CHOH group with the proviso that at least one of $R^2$ and $R^3$ is an alkyl group having from 1 to 5 carbon atoms.

5. A compound formula

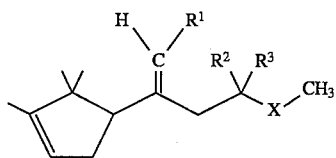

wherein $R^1$ is hydrogen or a methyl group, each of $R^2$ and $R^3$ is hydrogen or an alkyl group having from 1 to 5 carbon atoms, and X is CO or a CHOH group with the proviso that at least one of $R^2$ and $R^3$ is an alkyl group having from 1 to 5 carbon atoms.

6. A compound of claim 5 wherein each of $R^2$ and $R^3$ is independently an alkyl group having from 1 to 5 carbon atoms.

7. A compound of claim 6 wherein each of $R^2$ and $R^3$ is independently a methyl or an ethyl group.

8. A compound of the formula

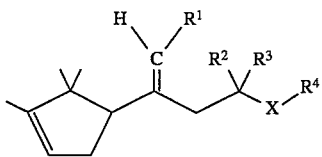

wherein $R^1$ is hydrogen or a methyl group, each of $R^2$ and $R^3$ is hydrogen or an alkyl group having from 1 to 5 carbon atoms, $R^4$ is hydrogen or $CHR^5R^6$ wherein each of $R^5$ and $R^6$ is hydrogen or an alkyl group having from 1 to 6 carbon atoms, and X is CO with the proviso that at least one of $R^2$ and $R^3$ is an alkyl group having from 1 to 5 carbon atoms.

9. A compound of claim 8 wherein each of $R^2$ and $R^3$ is independently an alkyl group having from 1 to 5 carbon atoms.

10. A compound of formula

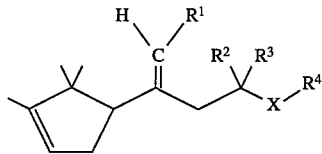

wherein $R^1$ is hydrogen or a methyl group, each of $R^2$ and $R^3$ is hydrogen or an alkyl group having from 1 to 5 carbon atoms, $R^4$ is $CHR^5R^6$ wherein each of $R^5$ and $R^6$ is hydrogen or an alkyl group having from 1 to 6 carbon atoms, and X is CO or a CHOH group with the proviso that at least one of $R^2$ and $R^3$ is an alkyl group having from 1 to 5 carbon atoms.

11. A compound of claim 10 wherein each of $R^2$ and $R^3$ is independently an alkyl group having from 1 to 5 carbon atoms.

12. A fragrance composition comprised of from about 1% to about 70% by weight of a compound of claim 5.

13. A fragrance composition comprised of from about 1% to about 70% by weight of a compound of claim 8.

14. A fragrance composition comprised of from about 1% to about 70% by weight of a compound of claim 10.

* * * * *

UNITED STATES PATENT AND TRADEMARK OFFICE
CERTIFICATE OF CORRECTION

PATENT NO. : 5,504,066
DATED : Apr. 2, 1996
INVENTOR(S) : Markert et al.

It is certified that error appears in the above-identified patent and that said Letters Patent is hereby corrected as shown below:

In Col 5, line 30, "dthydrojasmonate" should read --dihydrojasmonate--.

In Col 10, claim 3, line 40, formula IV, "$R^6$" should read --$R^4$--.

Signed and Sealed this

Thirty-first Day of March, 1998

Attest:

BRUCE LEHMAN

*Attesting Officer*      *Commissioner of Patents and Trademarks*